United States Patent [19]

Okamoto et al.

[11] 4,279,639

[45] * Jul. 21, 1981

[54] N-(2-SUBSTITUTED-4-PYRIDYL)UREAS AND THIOUREAS AS WELL AS PLANT GROWTH REGULATORS CONTAINING SAME, AND METHOD FOR USING COMPOUNDS AS PLANT GROWTH REGULATORS

[75] Inventors: Toshihiko Okamoto, 1-7-19, Shinoharakita, Kohokuku, Yokohamashi, Kanagawa; Yo Isogai, 1-1-2-609, Kamiyoga, Setagayaku, Tokyo; Koichi Shudo, 2000-10-2-116 Kosugayacho, Totsukaku, Yokohamashi, Kanagawa, all of Japan; Soshiro Takahashi, Urawashi, Japan

[73] Assignees: Toshihiko Okamoto, Yokohama; Yo Isogai, Tokyo; Koichi Shudo, Yokohama; Susumu Sato, Tokyo, all of Japan

[ * ] Notice: The portion of the term of this patent subsequent to Mar. 18, 1997, has been disclaimed.

[21] Appl. No.: 62,850

[22] Filed: Aug. 1, 1979

[30] Foreign Application Priority Data

Nov. 2, 1978 [JP] Japan ................................ 53-135236

[51] Int. Cl.³ .................... A01N 43/40; C07D 213/75
[52] U.S. Cl. ........................................ 71/94; 546/286; 546/289; 546/292; 546/305; 546/306
[58] Field of Search ............... 546/292, 306, 305, 286, 546/289; 71/94

[56] References Cited

U.S. PATENT DOCUMENTS

| | | | |
|---|---|---|---|
| 3,367,309 | 4/1968 | Foster et al. | 546/292 |
| 3,404,152 | 10/1968 | Thiele et al. | 546/306 |
| 3,426,031 | 2/1969 | Fischback et al. | 546/305 |
| 3,467,753 | 9/1969 | Foster et al. | 424/263 |
| 3,682,934 | 8/1972 | Martin et al. | 546/292 |
| 4,062,856 | 12/1977 | Spicer et al. | 546/306 |
| 4,149,872 | 4/1979 | Pilgram | 71/94 |
| 4,193,288 | 3/1980 | Shudo et al. | 546/305 |

FOREIGN PATENT DOCUMENTS

| | | | |
|---|---|---|---|
| 2843722 | 4/1979 | Fed. Rep. of Germany | 546/305 |
| 1119515 | 7/1968 | United Kingdom | 546/305 |
| 1489879 | 10/1977 | United Kingdom | 546/305 |
| 1122662 | 8/1978 | United Kingdom | 546/305 |

OTHER PUBLICATIONS

Chemical Abstracts, vol. 76, 1972, item 113031y, abstracting Lesiak et al., "Rocz. Chem.", 1971, vol. 45, No. 11, 1967-1968, (Polish).
Chemical Abstracts, vol. 89, 1978, Item 210302p, abstracting Isogai et al., "Sci. Pap. Coll. Gen. Educ.", Univ. Tokyo (1978), vol. 28, No. 1, pp. 93-127, (English).
Chemical Abstracts, vol. 90, 1979, item 98437d, abstracting Takahashi et al., "Phytochemistry", (1978), vol. 17, No. 8, pp. 1201-1207, (English).
Okamoto et al., "Chemical and Pharmaceutical Bulletin:Tokyo", vol. (26), (1978), pp. 3250-3252.

*Primary Examiner*—Robert T. Bond
*Attorney, Agent, or Firm*—Sughrue, Rothwell, Mion, Zinn and Macpeak

[57] ABSTRACT

Plant growth and suppression regulators of the N-(2-substituted-4-pyridyl)urea and thiourea type are provided, which exhibit excellent cytokinin-like activities and are thus useful for regulating plant growth in various fashions, such as acceleration of growth when used in flowering or fruiting at a controlled time when used in small amounts, and controlling compositions such as sugar, alkaloids, etc. of plants, or suppression of plant growth when used in an amount higher than optimal for growth acceleration, etc.

9 Claims, No Drawings

N-(2-SUBSTITUTED-4-PYRIDYL)UREAS AND THIOUREAS AS WELL AS PLANT GROWTH REGULATORS CONTAINING SAME, AND METHOD FOR USING COMPOUNDS AS PLANT GROWTH REGULATORS

BACKGROUND OF THE INVENTION

1. Field of the Invention

The present invention relates to novel N-(2-substituted-4-pyridyl)ureas and thioureas, agricultural composition comprising such active ingredients and methods of treating plants therewith.

2. Brief Description of the Prior Art

In the agricultural and horticultural fields, attention has been directed to plant growth regulators which accelerate or suppress the growth of plants when used in trace amounts and which can regulate plants in desired conditions.

In particular, recently techniques for controlling plant growth utilizing the hormone activity of chemicals such as cytokinin or gibberellin have been heavily investigated. Plant growth regulators echibiting cytokinin-like hormonal activity (hereafter referred to as cytokinin hormone activity) can accelerate plant growth when used in very small amounts. On the other hand, plant growth can sometimes be suppressed when such chemicals are employed in excess amounts, i.e., in amounts over that effective to accelerate plant growth (sometimes referred to as overdose use).

Accordingly, while the terms "plant growth regulation" and "plant growth regulator" used herein refer primarily to acceleration, they sometimes refer to suppression of plant growth (in overdose use) in a broad sense. Such seemingly contrary activities by the plant growth regulator are characteristic of cytokinin activity. In this regard, herbicides for which cytokinin activity has clearly been established are not known, though some herbicides have been established to have auxin activity (The term "auxin" is a general or collective name for a kind of plant growth regulators).

Typical plant growth regulators known as having cytokinin hormone activity are 6-benzyladenine, kinetin and 4-pyridylphenylurea. Further, 2-chloro-4-pyridylphenylurea and -thiourea have been proposed by the present inventors in Ser. No. 947,468 filed Oct. 2, 1978. However, development of plant growth regulators having more improved effect is still desired.

SUMMARY OF THE INVENTION

An object of the present invention is to provide novel plant growth regulators which provide effects equivalent to or superior to known plant growth regulators, agricultural compositions comprising the same and a methods of controlling plant growth using the same.

The active compounds provided by this invention comprise N-(2-substituted-4-pyridyl)ureas and thioureas of the formula:

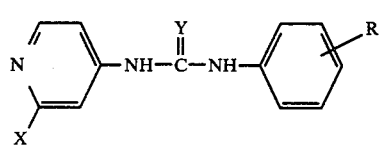

(I)

wherein X represents a fluorine atom, a bromine atom, a hydroxy group, a lower alkoxy group (having 1 to 6 carbon atoms, preferably 1 to 4 carbon atoms; hereafter the same, unless otherwise indicated, when the term "lower" is used to mean the alkyl moiety in any groups, e.g., the alkyl moiety in an alkoxycarbonyl group), a lower alkylthio group, a lower alkoxycarbonyl group, an amino group, a lower alkylcarbonylamino group, a benzoylamino group, a lower alkoxycarbonylamino group, a cyano group or a trifluoromethyl group; Y represents an oxygen atom or a sulfur atom; and R represents a hydrogen atom, a lower alkyl group, a lower alkoxy group, a hydroxy group, a halogen atom or a trifluoromethyl group.

DESCRIPTION OF PREFERRED EMBODIMENTS

The N-(2-substituted-4-pyridyl)ureas and thioureas of formula (I) in accordance with the present invention provide excellent physiological activities on plants similar to the effects provided by benzyladenine, such effects when used but exhibit in a far smaller amount.

More specifically, the compounds of the present invention can accelerate plant growth, cell mitosis, cell enlargement, cell differentiation, fruit bearing, flowering or fruiting or can promote such effects to occur at a desired time; regulate growth on plants at a desired level; prevent fruit from falling; prevent control compositions (e.g., sugar, alkaloids, etc.) of fruit or sugar cane; improve the taste of edible plants, etc.

By adjusting the amount of the compounds of the present invention employed, usually in the use of an overdose thereof, the compounds of the invention can conversely suppress plant growth to a desired level, with suppression of plant growth to an excessive degree generally being termed a herbicidal effect.

Thus, the plant growth regulators of the invention have a wide variety of practical features, e.g., not only can they promote or suppress plant growth but they also insure flowering or fruiting at a desired period of time, the formation of seedless fruit, maintain seeds in a dormant state or arouse seeds from a dormant state, prevent flowering or fruit plants and trees from shedding, prevent leaves from defoliating, etc.

Of the compounds of formula (I), particularly preferred are those wherein X represents OCH$_3$, F, Br or CF$_3$; Y represents O or S; and R represents F, Cl or CF$_3$. Specifically, N-(2-trifluoromethyl-4-pyridyl)-N'-(3-fluorophenyl)urea, N-(2-fluoro-4-pyridyl)-N'-phenylurea, N-(2-methoxy-4-pyridyl)-N'-phenylurea, N-(2-bromo-4-pyridyl)-N'-phenylurea, N-(2-trifluoromethyl-4-pyridyl)-N'-phenylurea, N-(2-methoxy-4-pyridyl)-N'-phenylthiourea, N-(2-carbomethoxy-4-pyridyl)-N'-phenylurea and N-(2-carbomethoxy-4-pyridyl)-N'-phenylthiourea are more preferred in the present invention.

The compounds of the present invention can be prepared according to the following reactions (a) and (b):

(a) Compounds of formula (II):

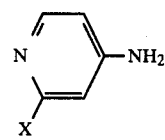

(II)

wherein X is as defined above are reacted with compounds of formula (III):

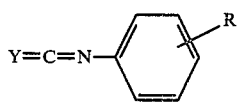

(III)

wherein Y and R are as defined above;
(b) Compounds of formulae (IV) or (IV'):

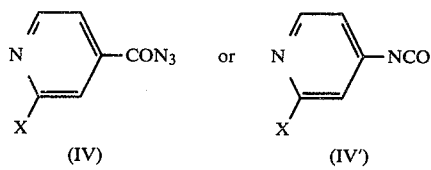

wherein X is as defined above (except X cannot be NH₂ and OH) are reacted with compounds of formula (V):

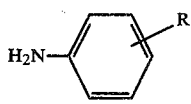

(V)

wherein R is defined as above.

If desired, the above reactions can be followed by hydrolysis, acylation or esterification in a conventional manner to convert the obtained substituent into a different desired substituent X. In the above, the compounds of formula (IV) are precursors of the compounds of formula (IV').

The aforementioned reactions (a) and (b) are performed in a conventional manner in the presence or absence of an organic solvent at room temperature or under heating.

Representative examples of organic solvents include benzene, acetone, pyridine, etc., which are particularly preferred. The use of anilines in an excess amount (at least 1.1 times) of anilines, which anilines are starting materials herein, as above defined, is advantageous since they also function as a solvent when used in excess.

While reaction conditions vary depending upon the product to be prepared, the conditions are generally as follows, unless otherwise indicated.

Reaction (a):
 temperature: below room temperature to about 100° C.
 reaction time: 10 mins.–30 hrs.
 pressure: usually atmospheric pressure
Reaction (b):
 Conversion of compounds of formula (IV) into compounds of formula (IV') usually requires a temperature of about 50° C. or more, preferably 50° to 150° C. The reaction of compounds of formula (IV') and the desired aniline(s) is generally performed at from room temperature to 100° C. Accordingly, a mixture of the compounds of formula (IV) and the desired aniline(s) is generally heated at a temperature of from 50° to 150° C. for about 30 mins. to about 10 hrs. Alternatively, a solution of the desired compound(s) (IV) is heated at 50° to 150° C. for about 30 mins. to about 10 hrs. and then the desired aniline(s) added thereto, followed by heating at a temperature from room temperature to 100° C.

Hydrolysis, acylation or esterification can then be performed to convert the substituents in the reaction products obtained by reactions (a) and (b) into other desired substituents in a conventional manner. Reaction conditions for these hydrolysis, acylation and esterification are briefly shown below as representative examples:

Hydrolysis:
Hydrolysis of, for example, alkoxy compounds is performed by heating with about 30% hydroiodic acid at about 100° C. in acetic acid. Acetamide compounds are hydrolyzed by heating with 6 N hydrochloric acid at about 100° C.

Acylation:
The corresponding amino or hydroxy compounds are reacted with acid anhydrides or acid chlorides at ambient temperature in a conventional manner.

Esterification:
Esterification is generally performed by heating with alcohols at 60° to 100° C. in the presence of an acid.

In the reactions referred to above, molar ratios of reactants are generally in equimolar ratio, unless otherwise indicated.

Of the starting materials of formulae (II), (III), (IV), (IV') and (V), compounds of formulae (III) and (V) are commercially available. Other compounds are prepared in a conventional manner, for example, as shown below.

Compound of formula (II):
The corresponding 4-nitro compounds or 4-nitropyridine N-oxides are reduced in the presence of metals such as Fe or Zn, or catalytically reduced to obtain compounds of formula (II).

Alternatively, compounds of formula (II) can also be prepared by hydrolyzing the corresponding azides or isocyanates.

Compound of formula (IV):
The corresponding carboxy compounds are converted into the corresponding hydrazides, followed by reacting with sodium nitrite.

Compound of formula (IV'):
Compounds of formula (IV) are heated under the conditions as set forth hereinabove.

The N-(2-substituted-4-pyridyl)ureas and thioureas in accordance with the present invention exhibit excellent biological activity on plants, particularly an excellent accelerating action on cell mitosis, cell enlargement, cell differentation, etc.; and are effective in accelerating fruiting, preventing fruit and flowers from falling, growth acceleration, weight increase of leaves, stalks, etc. retarding senescene, preventing chilling injury, etc. In addition, at a higher concentration, a marked suppression of growth (herbicidal activity) is exhibited, and, for example, the compounds of the present invention can be employed in herbicides or to prevent plant growth and germination.

Particularly preferred applications are to accelerate fruit on pepos such as melon, water melon, etc., prevent flower shedding with grapevines, weight increasing stalks and pots with lidney benas, etc., weight increasing leaves in Datura sunguina and tobacco plants, suppression of plant height, accelerating shoot growth of Datura, increasing the size of tobacco callus, growth of the leaf from tobacco callus, accelerating the proliferation of cultured cells, improving plant formation from callus, etc.

The compounds of the present invention can markedly accelerate cell mitosis, depending upon the concentration thereof in the medium used for the culture of plant cells, can be used in combination with other regulators such as auxin, etc. if desired, and can also markedly accelerate cell differentiation of stalks and leaves.

For example, the optimal concentration for accelerating cell mitosis of tobacco callus is as shown in the table below:

$$\underset{X}{\overset{N}{\diagdown}}\!\!\!\!\diagup\!\!\!\!\!\!\!\!-NH-\overset{\overset{Y}{\|}}{C}-NH-\!\!\!\!\diagdown\!\!\!\!\!\diagup\!\!\!\!-R$$

| No. | X | Y | R | Optimal Concentration (ppm) |
|---|---|---|---|---|
| 1 | Br | O | H | 0.05–0.0005 |
| 2 | F | " | " | 0.005–0.0005 |
| 3 | OCH$_3$ | " | " | 0.1–0.001 |
| 4 | NHCOCH$_3$ | " | " | –0.05 |
| 5 | CF$_3$ | " | " | 0.01–0.0005 |
| 6 | CF$_3$ | " | m-F | 0.001–0.0001 |
| 6-Benzyladenine | | | | 0.1–0.001 |

As is clear from the table above, compounds of the present invention is equivalent to or superior to 6-benzyladenine which is one of the most potent cytokinin compounds known in the art. In particular, Compound 1 is characteritic of its broad range of optimal concentration; this means easy handling of the chemical, i.e., no accidental withering of plants occurs even when used comparatively roughly: Compound 3 provides always excellent callus production: and Compound 6 provides effects in an extremely low amount.

Based on testing for tobacco callus shoot formation by cell differentiation, an amount of about 10 to about 100-fold of that given above is required.

The amount of the compounds of this invention used when applied by directly spraying plants is generally 10 to 100 liters per 10 ares as a solution of a concentration of 0.0001 to 10,000 ppm as effective ingredient, preferably 0.01 to 10,000 ppm. When applied to the soil, an amount 5 to 10 times that given above is required. It goes without saying, however, that the amount applied will differ according to the object of the control and the plant to which applied.

In general, 10 to 100 liters of a solution of the following concentration of the compound or compounds of the present invention, as active ingredient(s), is used per 10 area:

| | | Form Applied |
|---|---|---|
| For growth acceleration and increased fruiting | 0.01–1,000 ppm | directly to plant by, e.g., spraying, coating, dipping |
| For growth acceleration (proliferation or defferentiation of cultured cells) | 0.0001–100 ppm | cultured medium |
| For acceleration of fruit falling and defoliation | 0.1–10,000 ppm | directly to plant as shown above |
| For growth suppression and herbicide use | more than 10 –10,000 ppm | directly to plant as shown above, or to the soil |

The compounds of this invention can be used alone or in admixture with other substances or compositions effects desired during use, for example other plant regulatros, herbicides, insecticides, fungicides, and acaricides, typically in the form of solutions, emulsions, wettable powders, granules, fine granules, or powders.

The preparation of a suitable composition can be carried out in a conventional manner, e.g., by mixing 0.1 to 50%, preferably 0.1 to 10%, of a compound or compounds of this invention with a bulking agent, such as a liquid or solid diluent or carrier and, if desired or necessary, an emulsifying agent or dispersing agent.

Preferred liquid diluents or carriers include water, aromatic hydrocarbons such as xylene, benzene, and methylnaphthalene, chlorinated aromatic hydrocarbons such as chlorobenzene, mineral oil fractions such as paraffin, alcohols such as methanol and propanol, and polar solvents such as dimethylformamide and acetone.

Preferred solid diluents or carriers include, for example, talc, clay, kaolin, white carbon, wood powder and sand.

Preferred emulsifying agents include polyoxyethylene-fatty acid esters or polyoxyethylene-fatty acid alcohol ethers and preferred dispersing agents include alkyl sulfonates, alkyl aryl sulfonates, alkali metal slats, alkaline earth metal salts, ammonium salts of lignin-sulfonic acid, and methylcellulose.

The compounds of the present invention or preparations thereof per se may be added to a medium or applied directly to the plant or onto the surface of leaves or stalks thereof, or sprayed on the soil, they are usually applied in the form of a conventional preparation thereof. Further, the plant growth controlling agents of this invention may be applied together with conventional fertilizers and/or extenders.

The compounds of the present invention can also be used in the form of an inorganic or organic salt such as the hydrochloride phosphate, sulfate, citrate or tartarate, thereof.

The present invention will now be described in detail with reference to the examples below, but it is not to be deemed limited thereto.

Some representative examples of preparative forms will firstly be given below. Hereafter all percentages are weight percentages, unless otherwise indicated.

| Preparation 1. | Wettable powder | |
|---|---|---|
| | N-(2-Methoxy-4-pyridyl)-N'-phenylurea | 1% |
| | Sodium beta-naphthalenesulfonate-formaldehyde condensate | 2% |
| | Polyoxyethylene alkyl aryl ether | 2% |
| | Clay | 95% |
| Preparation 2. | Liquid | |
| | N-(2-Fluoro-4-pyridyl)-N'-phenylurea | 1% |
| | Dimethylformamide | 94% |
| | Polyoxyethylenesorbitan monolaurate | 5% |
| Preparation 3. | Solution | |
| | N-(2-Methoxy-4-pyridyl)-N'-phenylurea | 100 ppm |
| | Acetone | 20% |
| | Water | 80% |

The following Examples 1–11 show typical synthesis procedures for forming compounds of the present invention. Unless otherwise indicated, processing was at room temperature and at atmospheric pressure.

EXAMPLE 1

Synthesis of N-(2-methoxy-4-pyridyl)-N'-phenylurea

To a solution of 869 mg (7 mmol) of 2-methoxy-4-aminopyridine in dry benzene was added 834 mg (7 mmol) of phenyl isocyanate. After stirring the mixture at room temperature for 20 hrs., crystals precipitated which were removed by filtration and subjected to chromatography using alumina in a conventional manner. The column was developed with chloroform and the eluate containing the objective compound collected. Solvent was evaporated off under reduced pressure and the residue recrystallized from benzene to obtain 1.41 g. of N-(2-methoxy-4-pyridyl)-N'-phenylurea: yield 82.9%; m.p. 127°–129° C.

Elemental Analysis for $C_{13}H_{13}N_3O_2$:

|  | C | H | N |
| --- | --- | --- | --- |
| Calcd. (%) | 64.18 | 5.39 | 17.28 |
| Found (%) | 64.33 | 5.33 | 17.23 |

EXAMPLE 2

Synthesis of N-(2-hydroxy-4-pyridyl)-N'-phenylurea 2.5 ml. of glacial acetic acid and 3.5 ml. of about 30% hydroiodic acid were added to 272 mg (1.1 mmol) of N-(2-methoxy-4-pyridyl)-N'-phenylurea. While stirring, the mixture was then heated at 95° C. for 5.5 hrs. After cooling, solvent was removed by distillation. A small amount of water was added to the resulting residue which was then neutralized with ammonium carbonate. The crystals which precipitated were separated by filtration and recrystallized from ethanol to give 210 mg. of N-(2-hydroxy-4-pyridyl)-N'-phenylurea: yield 82.0%; m.p. 198°–200° C.

Elemental Analysis for $C_{12}H_{11}N_3O_2 \cdot H_2O$:

|  | C | H | N |
| --- | --- | --- | --- |
| Calcd. | 58.29 | 5.30 | 17.00 |
| Found | 58.20 | 5.28 | 16.94 |

EXAMPLE 3

Synthesis of N-(2-acetamido-4-pyridyl)-N'-phenylurea
35 ml. of dry acetone was added to 255 mg (1.7 mmol) of 2-acetamido-4-aminopyridine and the mixture was warmed to dissolve the aminopyridine. 201 mg (1.7 mmol) of phenyl isocyanate was then added to the resulting solution and the mixture then refluxed for 9 hrs. with stirring. After cooling, solvent was removed by distillation and the remaining residue subjected to chromatography in a conventional manner using silica gel. After developing the column with a chloroform-acetone (3:1 by volume) mixture, the eluate containing the objective compound was collected. After distilling solvent off under reduced pressure, the residue was recrystallized from an acetone- n-hexane solvent mixture to give 320 mg. of the objective compound; yield 70.2%; m.p. 188.5°–190° C.

Elemental Analysis for $C_{14}H_{14}N_4O_2$:

|  | C | H | N |
| --- | --- | --- | --- |
| Calcd. | 62.21 | 5.22 | 20.73 |
| Found | 62.51 | 5.25 | 20.59 |

EXAMPLE 4

Synthesis of N-(2-amino-4-pyridyl)-N'-phenylurea 15 ml of 6 N hydrochloric acid was added to 173 mg (0.64 mmol) of N-(2-acetamido-4-pyridyl)-N'-phenylurea. The mixture was then stirred for 6 hrs. on a boiling water bath. After cooling, the crystals which deposited were removed by filtration and a small amount of water added thereto to dissolve the crystals while warming. An aqueous sodium carbonate solution was then added to the solution to neutralize the same. The crystals which deposited were collected by filtration and recrystallized from methanol to give 98 mg. of the objective compound; yield 67.1%; m.p. above 290° C.

Elemental analysis for $C_{13}H_{12}N_4O$:

|  | C | H | N |
| --- | --- | --- | --- |
| Calcd. | 63.15 | 5.30 | 24.55 |
| Found | 62.85 | 5.27 | 24.60 |

EXAMPLE 5

Synthesis of N-(2-fluoro-4-pyridyl)-N'-phenylurea 112 mg (1 mmol) of 2-fluoro-4-aminopyridine was added to 9 ml of dry benzene and to the resulting solution was further added 119 mg (1 mmol) of phenyl isocyanate. After stirring at room temperature for 30 hrs., the crystals which deposited were collected by filtration and then subjected to chromatography in a conventional manner using alumina. After developing the column with a benzene-ethyl acetate (3:1 by volume) solvent mixture, eluate containing the objective compound was collected. After distilling solvent off under reduced pressure, the residue was recrystallized from an ethyl acetate-n-hexane solvent mixture to give 113 mg of the objective compound: yield 48.9%; m.p. 179°–180° C.

Elemental analysis for $C_{12}H_{10}F\ N_3O$:

|  | C | H | N | F |
| --- | --- | --- | --- | --- |
| Calcd. | 62.33 | 4.36 | 18.17 | 8.22 |
| Found | 62.49 | 4.36 | 18.11 | 8.15 |

EXAMPLE 6

Synthesis of N-(2-bromo-4-pyridyl)-N'-phenylurea

2-Bromo-4-aminopyridine (433 mg, 2.5 mmol) was added to 15 ml of dry benzene and the mixture warmed to dissolve the pyridine. 298 mg (2.5 mmol) of phenyl isocyanate was added to the solution and the resulting mixture stirred at room temperature for 20 hrs. The crystals which formed were collected by filtration and subjected to chromatography in a conventional manner using alumina. After developing the column with a benzene-ethyl acetate (2.5:1 volume) solvent mixture, the eluate containing the objective compound was collected. After distilling solvent off under reduced pressure, the residue was recrystallized from 70% methanol to give 308 mg of N-(2-bromo-4-pyridyl)-N'-phenylurea: yield 42.1%; m.p. 188°–189° C.

Elemental Analysis for $C_{12}H_{10}BrN_3O$:

|  | C | H | N |
|---|---|---|---|
| Calcd. | 49.34 | 3.45 | 14.38 |
| Found | 49.04 | 3.47 | 14.10 |

EXAMPLE 7

Synthesis of
N-(2-trifluoromethyl-4-pyridyl)-N'-phenylurea 31 mg (0.33 mmol) of aniline was added to a solution of 72 mg (0.33 mmol) of 2-trifluoromethylisonicotinoyl azide in 5 ml of dry benzene. The resulting mixture was refluxed for 4 hrs. while stirring. After cooling, solvent was removed by distillation and the residue chromatographed in a conventional manner using silica gel (solvent:CHCl₃:acetone=10:1 volume). Fractions were collected and solvent again removed by distillation. The residue was recrystallized from ethyl acetate-n-hexane to obtain the desired product in an amount of 80 mg (yield 85.1%); m.p. 169°–171° C.

IR spectrum (KBr): 3400 (—NH—) 1733 (—CO—).
Mass spectrum M+ (m/e): 281.
Elemental analysis for $C_{13}H_{10}N_3F_3O$:

|  | C | H | N | F |
|---|---|---|---|---|
| Calcd. | 55.52 | 3.58 | 14.94 | 20.27 |
| Found | 55.58 | 3.57 | 14.96 | 20.34 |

EXAMPLE 8

Synthesis of
N-(2-trifluoromethyl-4-pyridyl)-N'-(3-fluorophenyl)-urea

In a manner similar to Example 7, the desired product having a melting point of 165°–167° C. was obtained in an amount of 101 mg (yield 91.0%).

IR spectrum (KBr): 1738 (—CO—).
Mass spectrum M+ (m/e): 299.
Elemental analysis for $C_{13}H_9N_3F_4O$:

|  | C | H | N | F |
|---|---|---|---|---|
| Calcd. | 52.18 | 3.03 | 14.04 | 25.40 |
| Found | 52.12 | 2.96 | 13.76 | 24.92 |

EXAMPLE 9

Synthesis of
N-(2-carbomethoxy-4-pyridyl)-N'-phenylurea 146 mg of phenyl isocyanate was added to a solution of 186 mg (1.2 mmol) of methyl 4-aminopicolate in 4 ml of dry acetone. The resulting mixture was agitated at room temperature overnight. Solvent was then evaporated off and the residue chromatographed in a conventional manner using silica gel (solvent:CHCl₃:acetone=4:1 volume). Fractions were collected and solvent removed by distillation. The residue was recrystallized from methanol to give the desired product having a melting point of 206°–208° C. (decompd.) in an amount of 261 mg (yiled 78.6%).

IR spectrum (KBr): 1728, 1697 (—NHCONH—) and (—COOCH₃).
Mass spectrum M+ (m/e): none.
Elemental analysis for $C_{14}H_{13}N_3O_3$:

|  | C | H | N |
|---|---|---|---|
| Calcd. | 61.98 | 4.83 | 15.49 |
| Found | 61.83 | 4.85 | 15.24 |

EXAMPLE 10

Synthesis of
N-(2-methoxy-4-pyridyl)-N'-phenylthiourea 203 mg (1.5 mmol) of phenyl isothiocyanate was added to a solution of 186 mg (1.5 mmol) of 2-methoxy-4-aminopyridine in 15 ml of dry acetone. The mixture was then refluxed for 33 hrs. After cooling, solvent was evaporated off by distillation and the residue was chromatographed in a conventional manner using silica gel (solvent, CHCl₃:acetone=10:1 volume). Fractions were collected and solvent removed by distillation. The residue was recrystallized from ether to give the desired product having a melting point of 138°–141° C. in an amount of 130 mg (yield 33.4%).

Mass spectrum M+ (m/e): 259.
Elemental analysis for $C_{13}H_{13}N_3OS$:

|  | C | H | N |
|---|---|---|---|
| Calcd. | 60.21 | 5.05 | 16.20 |
| Found | 60.34 | 5.07 | 16.34 |

EXAMPLE 11

Synthesis of
N-(2-carbomethoxy-4-pyridyl)-N'-phenylthiourea 166 mg (1.2 mmol) of phenyl isothiocyanate was added to a solution of 187 mg (1.2 mmol) of methyl 4-aminopicolate in 4 ml of dry acetone. The mixture was then refluxed for 30 hrs. After cooling, solvent was removed by distillation and the residue chromatographed in a conventional manner using silica gel (solvent:CHCl₃:acetone=8:1 volume). Fractions were collected and solvent was removed by distillation. The residue was recrystallized from ethyl acetate to give the product having a melting point of 148°–149° C. in an amount of 141 mg (yield 39.9%).

IR spectrum (KBr): 1723 (—CO—).
Mass spectrum M+ (m/e): 287.
Elemental analysis for $C_{14}H_{13}N_3O_2S$:

|  | C | H | N |
|---|---|---|---|
| Calcd. | 58.52 | 4.56 | 14.62 |
| Found | 58.52 | 4.65 | 14.33 |

The following examples illustrate typical uses of the compounds of the present invention.

EXAMPLE 12

Growth Effect Test:
N-(2-fluoro-4-pyridyl)-N'-phenylurea on Tobacco Callus Cells Tobacco callus was cultured in Murashige-skoog medium containing 0.0001 to 0.1 ppm of N-(2-fluoro-4- pyridyl)-N'-phenylurea and 2 ppm of indolacetic acid for 30 days at 26° C. The final weight of fresh (not dried) callus is given in Table 1 below. The control was tobacco callus cultured in the Murashige-Skoog medium containing indolacetic acid alone, otherwise the conditions were identical. For the purpose of comparison, values obtained in a medium containing an optimal amount of benzyladenine are also given in Table 1. Values are an average of six runs. The measurement was in accordance with Torigai et al, Phytochemistry, vol. 11, page 1623 (1972).

TABLE 1

|  | Concentration (ppm) | Weight (g) |
|---|---|---|
| Compound of Invention | 0.0001 | 1.9 |
| " | 0.001 | 5.5 |
| " | 0.01 | 4.5 |
| " | 0.1 | 1.2 |
| Benzyladenine | 0.01 | 5.4 |
| " | 0.001 | 1.0 |
| Control | — | 0.2 |

It can be clearly seen that the compound of the invention provided a similar product yield at 0.001 ppm concentration to that obtained with benzyladenine at 0.01 ppm concentration. 0.001 ppm concentration of benzyladenine provided a far lower product yield than with the compound of the invention.

EXAMPLE 13

In a manner identical to Example 12, the tobacco callus growth test was performed except for using N-(2-methoxy-4-pyridyl)-N'-phenylurea. The results obtained are shown in Table 2 below.

TABLE 2

| Compound | Concentration (ppm) | Weight (g) |
|---|---|---|
| Compound of Invention | 0.0001 | 0.5 |
| " | 0.001 | 2.1 |
| " | 0.01 | 6.7 |
| " | 0.1 | 2.7 |
| Benzyladenine | 0.01 | 5.7 |
| Control | — | 0.2 |

The results show that the optimal concentration of the compound of the invention is almost the same as that of benzyladenine but provides better product yield.

EXAMPLE 14

Shoot Formation Test: Effect of N-(2-fluoro-4-pyridyl)-N'-phenylurea on Pith Tissue Section(s) of tobacco pith tissue were inoculated in Murashige-Skoog medium containing 0.01 to 10 ppm of N-(2-fluoro-4-pyridyl)-N'-phenylurea (containing no auxin). The system was cultured at room temperature for 30 days, and the number of pith sections forming shoots measured. The results obtained are shown in Table 3 below.

TABLE 3

| Compound | Concentration (ppm) | Shoot Formation Rate* |
|---|---|---|
| Compound of Invention | 10 | 12/12 |
| " | 1 | 12/12 |
| " | 0.1 | 7/12 |
| " | 0.01 | 0/12 |
| Benzyladenine | 1 | 7/12 |

*number of shoot bearing calluses/number of total calluses

EXAMPLE 15

Increase in Size of Leaves of Green Vegetable Test: N-(2-methoxy-4-pyridyl)-N'-phenylurea A leaf of *Brassica repa var. pervidis* which had been cut into rount sections with a crokborer was floated on the surface of water containing the above-identified compound to insure contact between the water and the back of the leaf sections. The system was allowed to stand for 8 days at room temperature. Thereafter, the diameter and weight of the leaf sections were determined. The results are shown in Table 4 below wherein all values are an average of 10 pieces of leaf section. Control contained only water.

TABLE 4

| Concentration (ppm) | Diameter (mm) | Weight (mg) |
|---|---|---|
| 10 | 15.2 | 30.8 |
| 1 | 15.3 | 32.0 |
| 0.1 | 16.8 | 34.0 |
| 0.01 | 17.2 | 36.0 |
| 0.001 | 14.8 | 30.3 |
| Control | 12.8 | 27.5 |

As is clearly seen from the results in the table above, the most optimal concentration of the compound of the invention is 0.01 ppm, and both the diameter and weight of the leaf increased by about 30% as compared to control.

EXAMPLE 16

Effect of N-(2-methoxy-4-pyridyl)-N'-phenylurea on Young Cucumbers

An aqueous solution containing 10 to 100 ppm of the above-identified compound was sprayed on cucumber planted in pots having a diameter of 10 cm at the time when 3 to 4 leaves were out. The height, stalk diameter and weight over the ground (stalks and leaves) were measured 15 days after the treatment. The results are shown in Table 5 below wherein the height, stalk diameter and weight over the ground of the plant are expressed by percentages, taking as 100% the corresponding values of an untreated plant (control). The values given are an average of 4 plants.

TABLE 5

| Concentration of Compound (ppm) | 10 | 50 | 100 |
|---|---|---|---|
| Height (%) | 95 | 91 | 91 |
| Diameter (%) | 100 | 110 | 118 |
| Weight (%) | 97 | 108 | 120 |

As is clearly seen from the results above, the stalk diameter could be increased on one hand, and, on the other hand, the height could be suppressed as compared to control. This indicates that the compound of the invention could provide plants which could resist strong wind and snow.

EXAMPLE 17

Effect of N-(2-bromo-4-pyridyl)-N'-phenylurea in Preventing Flower Shedding in Grapes Testing was performed with a grapevine (variety Delaware) planted in the field.

Flower clusters of the grapevine were dipped in aqueous solutions containing 100 ppm of gibberelline and 10 ppm or 100 ppm of the above identified compound at the time when the gibberelline treatment was optimal. Ten days after full bloom, all the flower clusters were again soaked and treated with an aqueous solution containing 100 ppm of gibberelline alone. Grapes were harvested 53 days thereafter and the effect of preventing flower shedding was measured. For comparison, the results obtained using, instead of the above identified compound, 100 ppm of benzyladenine are also shown in Table 6 below.

TABLE 6

|  | Gibberlline alone (control) | Compound of Invention | | Benzyladenine 100 ppm |
|---|---|---|---|---|
|  |  | 10 ppm | 100 ppm |  |
| Weight of Fruit Clusters (g) | 115 | 185 | 183 | 150 |
| Number of Fruit | 90 | 136 | 140 | 118 |

As is clearly seen from the results above, the compound of the invention obviously increased harvest of grapes.

EXAMPLE 18

Test on Increase of Weight and Supression of Height in Datura Sunguinea using N-(2-Methoxy-4-pyridyl)-N'-phenylurea Datura Sunghinea sp. (average height 8 cm) plants were transplanted outdoors. When the average height of the plants reached 20 cm, an aqueous solution of the above-identified compound in a concentration as shown in Table 7 below was sprayed onto the plants in an amount of 15 ml per plant. Three weeks later, the plants were harvested and the height of the plants and the total weight over the ground (stem and leaves) measured. The results are shown in Table 7 below wherein values are an average of five plants.

TABLE 7

| Compound | Concentration (ppm) | Height (cm) | Total Weight (g) |
|---|---|---|---|
| Compound of Invention | 100 | 91 | 385 |
|  | 200 | 89 | 391 |
| Benzyladenine | 500 | 98 | 330 |
| Control | — | 99 | 303 |

As can be seen from the results above, the amount harvested increased by about 30% as compared to that of benzyladenine.

What is claimed is:

1. A compound of the formula;

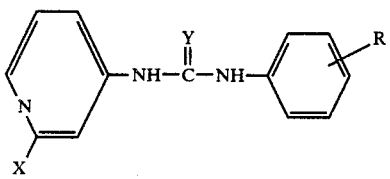

wherein X represents a member selected from the group consisting of fluorine, bromine, hydroxy, lower alkoxy, lower alkylthio, lower alkoxycarbonyl, amino, lower alkylcarbonylamino, benzoylamino, lower alkoxycarbonylamino, cyano and trifluoromethyl; Y represents a member selected from the group consisting of oxygen and sulfur; and R represents a member selected from the group consisting of hydrogen, lower alkyl, lower alkoxy, hydroxy, halogen and trifluoromethyl.

2. The compound of claim 1 wherein X represents a member selected from the group consisting of $OCH_3$, F, Br and $CF_3$ and R represents a member selected from the group consisting of F, Cl and $CF_3$.

3. The compound of claim 1 which is N-(2-trifluoromethyl-4-pyridyl)-N'-(3-fluorophenyl)urea.

4. The compound of claim 1 which is N-(2-fluoro-4-pyridyl)-N'-phenylurea.

5. The compound of claim 1 which is N-(2-methoxy-4-pyridyl)-N'-phenylurea.

6. The compound of claim 1 which is N-(2-bromo-4-pyridyl)-N'-phenylurea.

7. The compound of claim 1 which is N-(2-trifluoromethyl-4-pyridyl)-N'-phenylurea.

8. An agricultural composition useful as a plant growth regulator comprising as an active ingredient a compound of the formula:

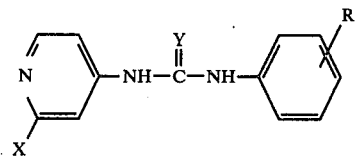

wherein X represents a member selected from the group consisting of fluorine, bromine, hydroxy, lower alkoxy, lower alkylthio, lower alkoxycarbonyl, amino, lower alkylcarbonylamino, benzoylamino, lower akoxycarbonylamino, cyano and trifluoromethyl; Y represents a member selected from the group consisting of oxygen and sulfur; and R represents a member selected from the group consisting of hydrogen, lower alkyl, lower alkoxy, hydroxy, halogen and trifluoromethyl, in an effective plant growth regulating amount, together with a carrier or diluent.

9. A method of controlling plant growth which comprises contacting a plant or a part thereof with a compound of the formula:

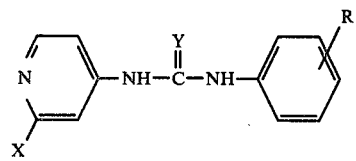

wherein X represents a member selected from the group consisting of fluorine, bromine, hydroxy, lower alkoxy, lower alkylthio, lower alkoxycarbonyl, amino, lower alkylcarbonylamino, benzoylamino, lower alkoxycarbonylamino, cyano and trifluoromethyl; Y represents a member selected from the group consisting of oxygen and sulfur; and R represents a member selected from the group consisting of hydrogen, lower alkyl, lower alkoxy, hydroxy, halogen and trifluoromethyl, in an amount effective for regulation of the growth of said plant.

* * * * *